United States Patent [19]

Hanai et al.

[11] Patent Number: 5,706,698
[45] Date of Patent: Jan. 13, 1998

[54] KNITTED YARNS DURABILITY TESTER WITH VIBRATION UNIT

[75] Inventors: Kiyoshi Hanai; Kanji Ishii, both of Toyota; Nobuaki Funahashi, Ichinomiya; Fumio Ikeda, Nagoya, all of Japan

[73] Assignees: Toyota Jidosha Kabushiki Kaisha; Toyoda Gosei Co., Ltd., both of Aichi-Ken, Japan

[21] Appl. No.: 684,094

[22] Filed: Jul. 19, 1996

[30] Foreign Application Priority Data

Oct. 30, 1995 [JP] Japan ................... 7-282176
Feb. 29, 1996 [JP] Japan ................... 8-43280

[51] Int. Cl.⁶ ........................................... G01L 5/06
[52] U.S. Cl. ..................... 73/160; 73/159; 73/796; 73/827
[58] Field of Search .............. 73/159, 160, 796, 73/827

[56] References Cited

U.S. PATENT DOCUMENTS 1,505,127  8/1924  Ayres ......................... 73/159
4,572,243  2/1986  Felix ......................... 73/160 X

FOREIGN PATENT DOCUMENTS 5-273115   10/1993  Japan.
953215     3/1964   United Kingdom.
1010669    11/1965  United Kingdom.
96/04100A1 2/1996   WIPO.

*Primary Examiner*—Elizabeth L. Dougherty
*Assistant Examiner*—Joseph L. Felber
*Attorney, Agent, or Firm*—Oliff & Berridge

[57] ABSTRACT

A tester for measuring a durability of a knitted yarn portion in which at least two sets of yarns, including a set of first yarns and a set of second yarns, are intersected, the tester includes: a first holding unit holding ends of the two sets of yarns at first positions that are relative to the knitted yarn portion; a second holding unit holding opposite ends of the two sets of yarns at second positions that are relative to the knitted yarn portion; and a position adjusting unit, connected to the first holding unit and the second holding unit, allowing at least one of the first positions and the second positions, relative to the knitted yarn portion, to be moved to other positions, thus varying an intersecting angle of the yarns of the knitted yarn portion.

10 Claims, 5 Drawing Sheets

KNITTED YARNS DURABILITY TESTER WITH VIBRATION UNIT

BACKGROUND OF THE INVENTION (1) Field of the Invention

The present invention generally relates to a knitted yarns durability tester, and more particularly to a knitted yarns durability tester for measuring a durability of a knitted yarn portion in which two sets of yarns are intersected at an intersecting angle, the knitted yarns durability tester capable of varying the intersecting angle between the sets of the yarns for each of test pieces.

(2) Description of the Related Art

Japanese Laid-Open Patent Application No. 5-273115 discloses a tensile strength tester for a glass-fiber fabric. The glass-fiber fabric is used as a base material of a printed circuit board. A yield stress of the glass-fiber fabric varies if the direction of the glass fiber in the fabric relative to the direction of the applied tension varies.

When measuring the tensile strength of test pieces of the glass-fiber fabric, it is necessary to predetermine an angle between the direction of the glass fiber and the direction of the applied tension. In the case of the above tensile strength tester, it is predetermined that the direction of the glass fiber is at angle of 45° to the direction of the applied tension force.

When the measurement of the tensile strength of a test piece is performed by using the above tensile strength tester, upper and lower holding parts hold both ends of the test piece. A tensile force is applied to the test piece in a longitudinal direction thereof by using the holding parts. The test piece of the glass-fiber fabric is prepared to have the glass fiber in a direction at an angle of 45° to the longitudinal direction of the test piece. Since the tensile force is applied to the test piece in the longitudinal direction thereof, the direction of the applied tensile force is at the angle of 45° to the direction of the glass fiber.

When the measurement of the tensile strength of the glass-fiber fabric is performed under the above testing condition, the result of the measurement obtained from the above tensile strength tester is accurate and reliable. However, it is necessary for the above tensile strength tester to prepare another test piece having a different glass-fiber direction in order to vary the angle between the direction of the applied tensile force and the direction of the glass fiber.

Generally, the physical property or durability of a knitted yarn portion in which two sets of yarns are intersected at an intersecting angle vary depending on the intersecting angle between the sets of yarns. Accordingly, in order to provide an adequate level of the durability of the knitted yarn portion, it is necessary to determine an optimal value of the intersecting angle for the knitted yarn portion by measuring individual durabilities of a number of different test pieces having different intersecting angles and analyzing the results of the durability measurement.

However, in order to carry out the durability measurement by using the above tensile strength tester, it is necessary to prepare a number of test pieces of knitted yarn portion having different intersecting angles prior to the durability measurement. It is difficult for the above tensile strength tester to carry out the durability measurement in order to determine the optimal value of the intersecting angle for the knitted yarn portion.

SUMMARY OF THE INVENTION

An object of the present invention is to provide a novel and useful knitted yarns durability tester in which the above-described problems are eliminated.

Another object of the present invention is to provide a knitted yarns durability tester which allows the intersecting angle between the yarns of a knitted yarn portion to be easily varied while the sets of the yarns of the knitted yarn portion are held at separate positions.

The above-mentioned objects of the present invention are achieved by a tester for measuring a durability of a knitted yarn portion in which at least two sets of yarns, including a set of first yarns and a set of second yarns, are intersected, which tester includes: a first holding unit holding ends of the above at least two sets of yarns at first positions that are relative to the knitted yarn portion; a second holding unit holding opposite ends of the above at least two sets of yarns at second positions that are relative to the knitted yarn portion; and a position adjusting unit, connected to the first holding unit and the second holding unit, allowing at least one of a position of the first holding unit and a position of the second holding unit, both relative to the knitted yarn portion, to be changed, so that an intersecting angle between the yarns of the knitted yarn portion is varied.

When the knitted yarns durability tester of the present invention is used to perform the durability measurement, it is possible to easily vary the intersecting angle between the sets of yarns of the knitted yarn portion. Therefore, it is unnecessary to prepare, prior to the durability measurement, a number of test pieces of the knitted yarn portion which have different intersecting angles respectively. In addition, it is possible for the knitted yarns durability tester of the present invention to efficiently and precisely measure individual durabilities of different test pieces having different intersecting angles. Therefore, it is possible to determine the optimal value of the intersecting angle for the knitted yarn portion from the results of the durability measurement.

BRIEF DESCRIPTION OF THE DRAWINGS

The above and other objects, features and advantages of the present invention will become more apparent from the following detailed description when read in conjunction with the accompanying drawings in which.

DETAILED DESCRIPTION OF THE PREFERRED EMBODIMENTS

A description will now be given of the preferred embodiments of the present invention with reference to the accompanying drawings.

Knitted yarns durability testers in the following embodiments of the present invention which are used to carry out the durability measurement of knitted yarn portions of automotive brake hoses will be described.

Figure 1:
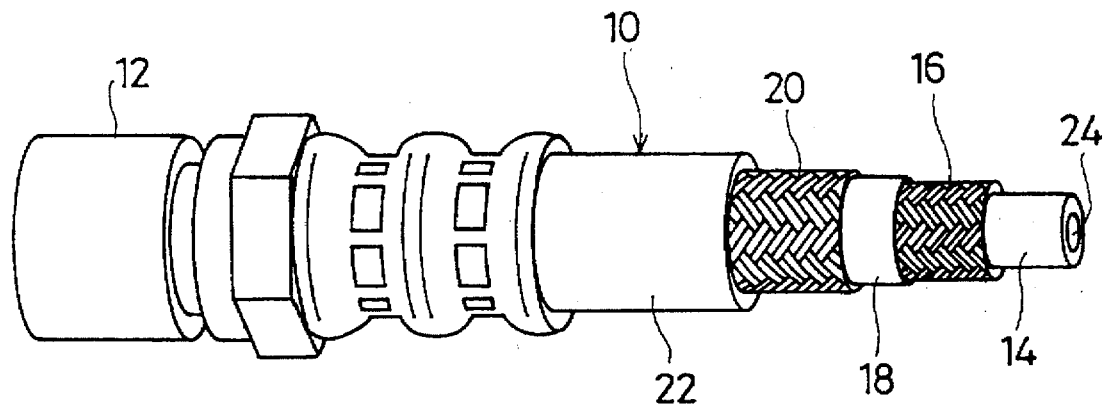
FIG. 1 is a perspective view of an automotive brake hose including knitted yarn portions.

FIG. 1 shows an automotive brake hose 10 including knitted yarn portions.

Referring to FIG. 1, a joint 12 which is used to connect the brake hose 10 to a hydraulic circuit of an automotive braking system is attached to one end of the brake hose 10. The joint 12 is a hollow member of metallic material and has a hydraulic passage provided therein. The brake hose 10 generally has an inner rubber hose 14, a reinforcing knitted yarn portion 16, an intermediate rubber hose 18, a reinforcing knitted yarn portion 20, and an outer rubber hose 22. The inner rubber hose 14 includes a hydraulic passage 24. The hydraulic passage 24 of the inner rubber hose 14 and the hydraulic passage of the joint 12 communicate with each other, and brake fluid under pressure is filled in and fed through these hydraulic passages of the brake hose 10.

In order to easily handle the brake hose 10 when it is assembled in the automotive vehicle, and in order to ensure a smooth steering action of the steering wheel on the vehicle, it is required that the brake hose 10 has an adequate level of bending strength. On the other hand, in order to efficiently transmit the pressure of brake fluid to the wheel cylinder through the brake hose 10, it is required that the brake hose 10 has a coefficient of volumetric expansion below a given reference value that is the upper limit of the coefficient of volumetric expansion capable of maintaining the hydraulic passage 24 of the brake hose 10 at an appropriate inside diameter.

To meet both the above requirements, it is desirable for the knitted yarn portions 16 and 20 of the brake hose 10 to flexibly resist to the bending deformation of the brake hose 10 and to reliably prevent the radial expansion of the hydraulic passage 24 of the brake hose 10.

The high-pressure brake fluid is fed through the hydraulic passage 24 of the brake hose 10 each time a braking action of the automotive vehicle is performed. When the feeding of the high-pressure brake fluid through the hydraulic passage 24 is repeated, the stresses to expand the inside diameter of the hydraulic passage 24 act on the knitted yarn portions 16 and 20 of the brake hose 10 in a repetitive manner. Since such stresses are applied to the knitted yarn portions 16 and 20 in a repetitive manner, the yarns included in the knitted yarn portions 16 and 20 are subjected to the repeated tension and slacking, and the repeated friction between the yarns is caused.

If some local areas of the knitted yarn portions 16 and 20 are damaged due to the repeated tension and slacking and/or the repeated friction, the corresponding areas of the brake hose 10 become extremely weak. The brake hose 10 in such a case may cause the response of the vehicle when it is braked to be poor. In order to avoid the problem, it is further required that each of the yarns of the knitted yarn portions 16 and 20 has an adequate level of durability or resistance to wear, fatigue and shearing, in addition to the previously-mentioned requirements of the brake hose 10.

The physical property or durability of the knitted yarn portion in which two sets of yarns are intersected at an intersecting angle vary depending on the intersecting angle between the sets of yarns. Accordingly, in order to provide an adequate level of the durability of the knitted yarn portion, it is necessary to determine an optimal value of the intersecting angle for the knitted yarn portion by measuring individual durabilities of a number of different test pieces having different intersecting angles and analyzing the results of the durability measurements.

Figure 2:
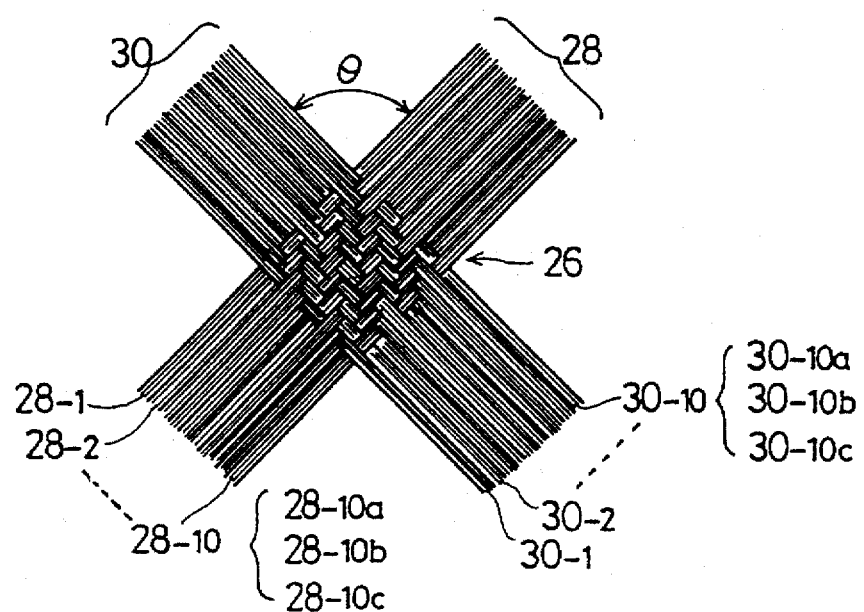
FIG. 2 is an enlarged view of a test piece which is subjected to durability measurement by a knitted yarns durability tester of the present invention.

FIG. 2 shows a test piece which is subjected to the durability measurement by a knitted yarns durability tester according to the present invention.

Referring to FIG. 2, the test piece has a knitted yarn portion 26 in which a set of first yarns 28 and a set of second yarns 30 are intersected. The first yarns 28 and the second yarns 30 in the knitted yarn portion 26 are interlaced in a predetermined pattern. In addition, as shown in FIG. 2, the first yarn set and the second yarn set intersect each other at an intersecting angle Θ.

In the present embodiment, the first yarn set includes ten yarns 28-1 through 28-10, and the second yarn set includes ten yarns 30-1 through 30-10. The yarns 28-1 through 28-10 and the yarns 30-1 through 30-10 are made of the same material. Each of the yarns 28-1 through 28-10 and the yarns 30-1 through 30-10 is a strand of three twisted threads. For example, the yarn 28-10 is a strand of three twisted threads 28-10$a$, 28-10$b$, and 28-10$c$.

When the test piece shown in FIG. 2 is set on the knitted yarns durability tester of the present invention, the yarns of the first yarn set and the yarns of the second yarn set are held by a first yarn holding unit and held by a second yarn holding unit. The knitted yarns durability tester of the present invention is capable of varying at least one of the position of the first yarn holding unit relative to the test piece and the position of the second yarn holding unit relative to the test piece, which will be described below.

Therefore, the knitted yarns durability tester of the present invention is capable of varying the intersecting angle Θ between the sets of the yarns by changing the position of the first yarn holding unit and/or the position of the second yarn holding unit relative to the knitted yarn portion. Hence, it is possible to easily carry out the durability measurement for different test pieces having different intersecting angles, in order to determine the optimal value of the intersecting angle for the knitted yarn portion. It is unnecessary to prepare a number of test pieces having different intersecting angles prior to the durability measurement.

Next, a description will be given of a knitted yarns durability tester 32 in one embodiment of the present invention with reference to FIG. 3 through FIG. 6.

Figure 3:
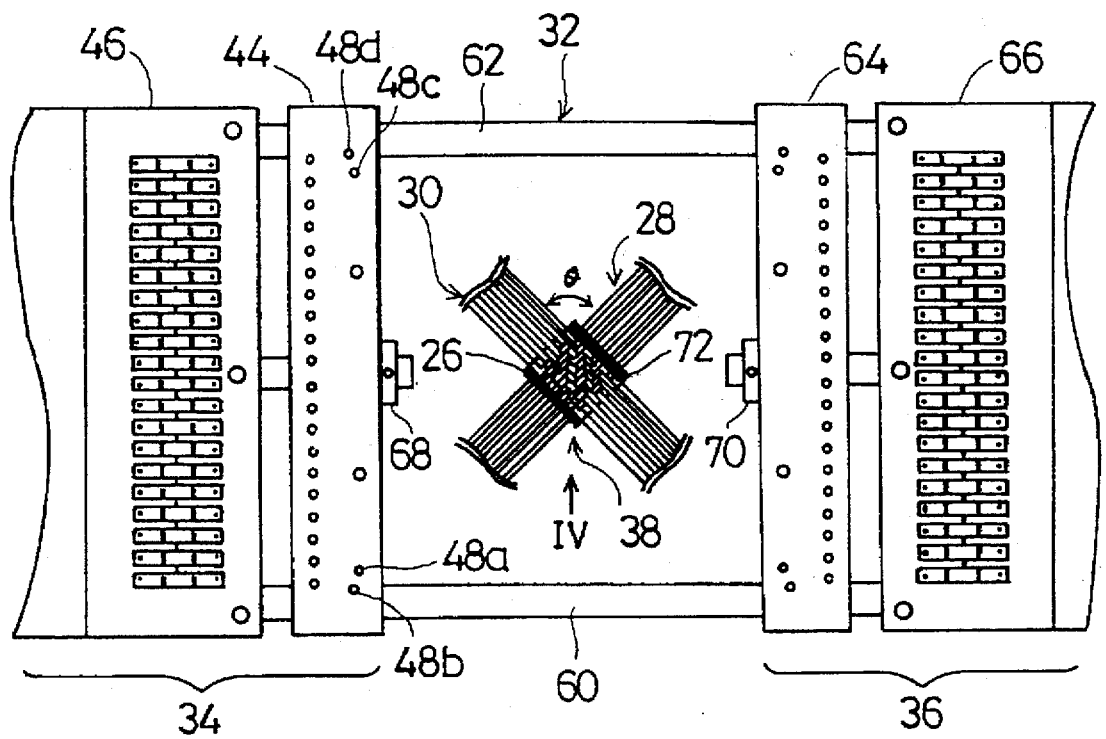
FIG. 3 is a plan view of a knitted yarns durability tester in one embodiment of the present invention.

Referring to FIG. 3, the knitted yarns durability tester 32 includes a yarn holding unit 34, a yarn holding unit 36, and a vibration unit 38. The yarn holding unit 34 holds ends of the first yarns 28 and ends of the second yarns 30 at first positions relative to the knitted yarn portion 26. The first positions are located on the left side of the knitted yarns durability tester 32. The yarn holding unit 36 holds the opposite ends of the first yarns 28 and the opposite ends of the second yarns 30 at second positions relative to the knitted yarn portion 26. The second positions are located on the right side of the knitted yarns durability tester 32. The vibration unit 38 subjects the knitted yarn portion 26 to vibrations in the up and down vertical directions.

Figure 4:
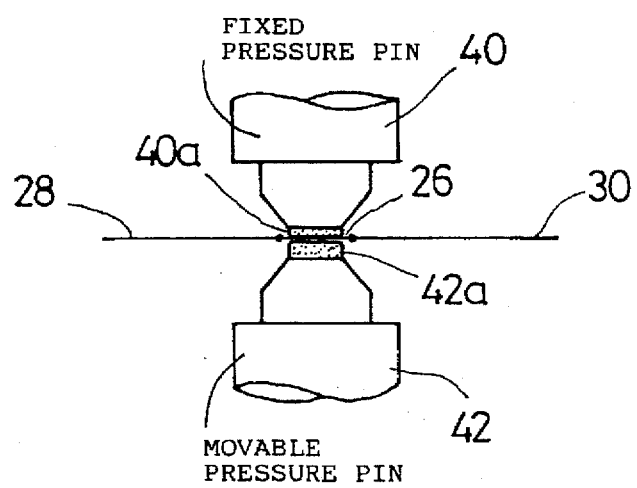
FIG. 4 is a side view of a vibration part of the knitted yarns durability tester when viewed in a direction indicated by arrow IV in FIG. 3.

FIG. 4 is a side view of the vibration unit 38 of the knitted yarns durability tester 32 when viewed in a direction indicated by arrow IV in FIG. 3.

Referring to FIG. 4, the vibration unit 38 generally has a fixed pressure pin 40 and a movable pressure pin 42. The fixed pressure pin 40 is placed on the knitted yarn portion 26 of the test piece, and the movable pressure pin 42 is placed beneath the knitted yarn portion 26.

The fixed pressure pin 40 has a rubber pad 40$a$ at the lower edge of the pin 40. The rubber pad 40$a$ is brought into contact with a top surface of the knitted yarn portion 26. The fixed pressure pin 40 is secured to the knitted yarns durability tester 32.

The movable pressure pin 42 is connected to a vibration source (not shown) of the knitted yarns durability tester 32. The movable pressure pin 42 has a rubber pad 42a at the upper edge of the pin 42, and the rubber pad 42a is placed beneath the knitted yarn portion 26. The movable pressure pin 42 is moved up and down by the vibrating source so that the movable pressure pin 42 is capable of transmitting the vibrations to the knitted yarn portion 26 against the fixed pressure pin 40. Thus, the vibration unit 38 subjects the knitted yarn portion 26 to the vibrations via the rubber pads 40a and 42a.

In the present embodiment, the position of the movable pressure pin 42 beneath the knitted yarn portion 26 is preset such that there is a predetermined clearance between the rubber pad 42a and the knitted yarn portion 26 when the movable pressure pin 42 is at its lower dead center.

The rubber pad 40a and the rubber pad 42a in the vibration unit 38 have a modulus of elasticity which is essentially the same as the modulus of elasticity of the rubber hoses 14, 18 and 22 of the brake hose 10. The condition in which the knitted yarn portion 26 of the test piece is subjected to the vibrations by the movable pressure pin 42 is approximately the same as the condition in which the knitted yarn portions 16 and 20 of the brake hose 10 on the vehicle are subjected to the stresses to expand the inside diameter of the hydraulic passage 24 when the brake fluid is fed through the brake hose 10.

Figure 5:
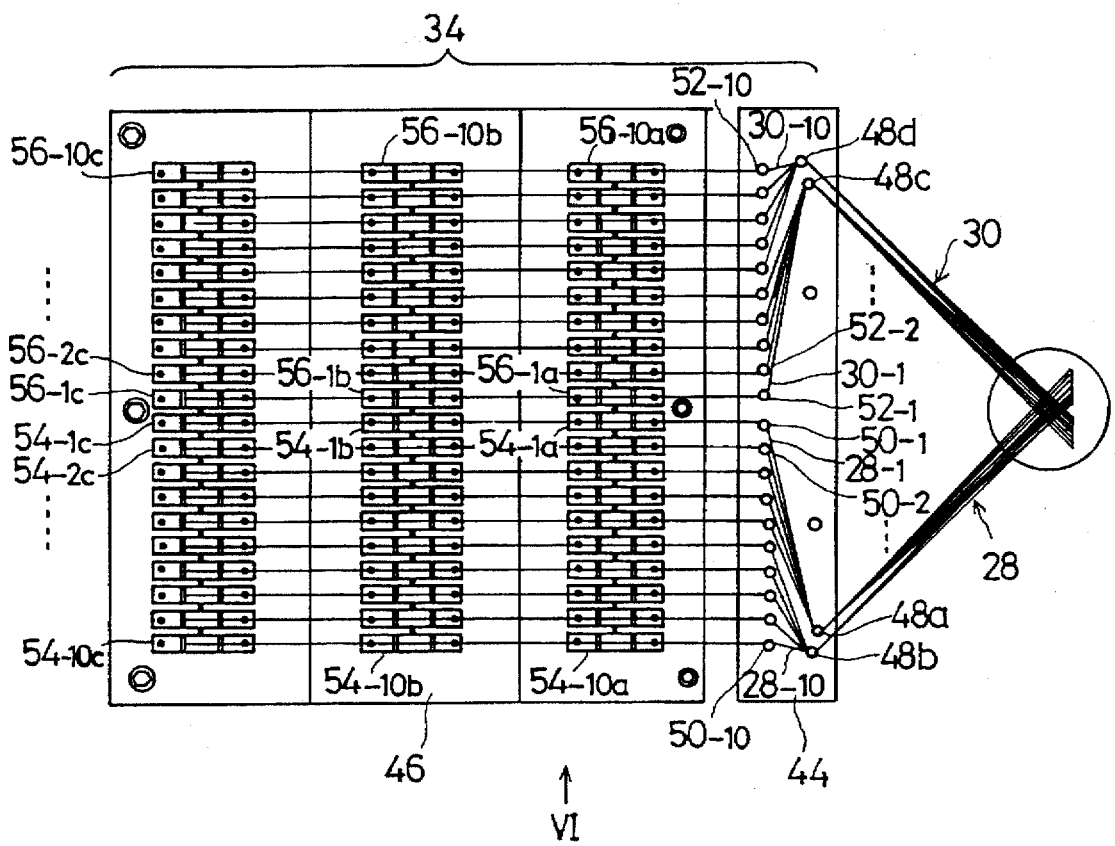
FIG. 5 is a plan view of a yarn holding unit of the knitted yarns durability tester in FIG. 3.
Figure 6:
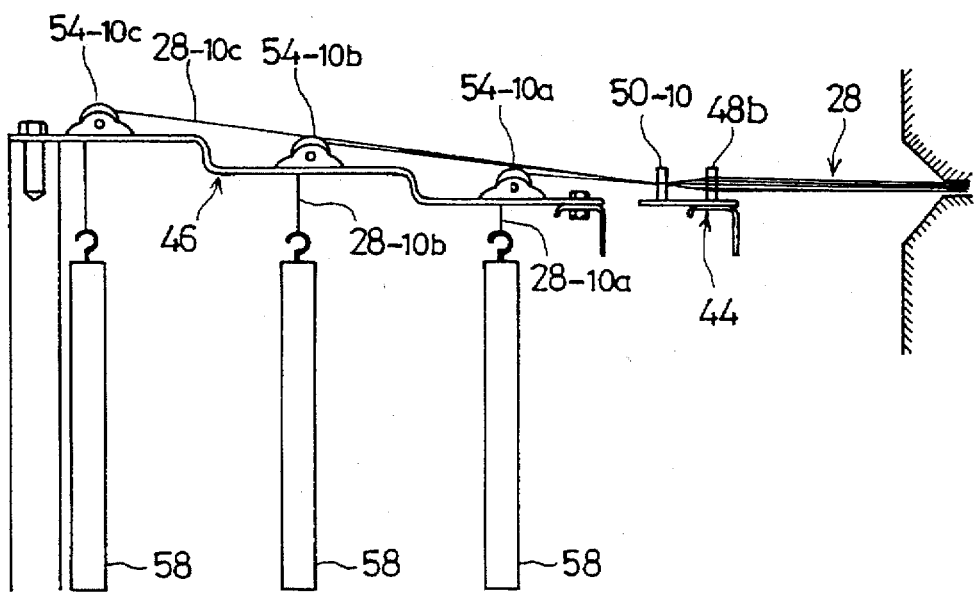
FIG. 6 is a side view of the yarn holding unit of the knitted yarns durability tester when viewed in a direction indicated by arrow VI in FIG. 5.

FIG. 5 is a plan view of the yarn holding unit 34 of the knitted yarns durability tester 32 in FIG. 3. FIG. 6 is a side view of the yarn holding unit 34 when viewed in a direction indicated by arrow VI in FIG. 5.

In the knitted yarns durability tester 32, the yarn holding unit 34 and the yarn holding unit 36 have essentially the same structure, and they are symmetrically arranged with respect to the position of the knitted yarn portion. For the sake of convenience, only the yarn holding unit 34 will be described in the following, and a description of the yarn holding unit 36 will be omitted.

Referring to FIG. 5, the yarn holding unit 34 includes a movable base 44 and a pulley base 46. The movable base 44 includes yarn pins 48a through 48d, yarn pins 50-1 through 50-10, and yarn pins 52-1 through 52-10. These yarn pins extend vertically from the top of the movable base 44. Similarly to the yarn holding unit 34, the yarn holding unit 36 includes a movable base 64 and a pulley base 66 as shown in FIG. 3.

The yarns 28-1 through 28-5, or one half of the yarns included in the first yarn set of the knitted yarn portion, are connected to or wound on the yarn pin 48a, and they are further connected to the yarn pins 50-1 through 50-5 separately. The yarns 28-6 through 28-10, or the remainder of the yarns of the first yarn set 28, are connected to or wound on the yarn pin 48b, and they are further connected to the yarn pins 50-6 through 50-10 respectively.

Similarly, the yarns 30-1 through 30-5, or one half of the yarns of the second yarn set 30, are connected to or wound on the yarn pin 48c, and they are further connected to the yarn pins 52-1 through 52-5 respectively. The yarns 30-6 through 30-10, or the remainder of the yarns of the second yarn set 30, are connected to or wound on the yarn pin 48d, and they are further connected to yarn pins 52-6 through 52-10 respectively.

Referring to FIG. 6, the pulley base 46 includes three rows of pulleys 54 which are arranged on the pulley base 46 at different heights, including: first-stage pulleys 54-1a through 54-10a; second-stage pulleys 54-1b through 54-10b; and third-stage pulleys 54-1c through 54-10c. The yarns 28-1 through 28-10 of the first yarn set 28 are wound on these pulleys 54.

The pulley base 46 further includes three rows of pulleys 56 which are similarly arranged on the pulley base 46 at different heights and are in parallel with the rows of the pulleys 54, including: first-stage pulleys 56-1a through 56-10a, second-stage pulleys 56-1b through 56-10b, third-stage pulleys 56-1c through 56-10c. The yarns 30-1 through 30-10 of the second yarn set 30 are wound on these pulleys 56.

As described above, each of the yarns 28-1 through 28-10 and the yarns 30-1 through 30-10 is a strand of three twisted threads. All the threads of the yarns from the knitted yarn portion 26 of the test piece are individually wound on the pulleys 54 and 56 on the pulley base 46. For example, the threads 28-10a, 28-10b and 28-10c of the yarn 28-10 are individually wound on the pulleys 54-10a, 54-10b and 54-10c.

As shown in FIG. 6, the yarn holding unit 34 includes a plurality of weights 58 which are tied to the leading edges of the threads from the yarns of the knitted yarn portion 26, respectively. The weights 58 provided in the yarn holding unit 34 correspond to the pulleys on the pulley base 46 one to one. The weights 58 corresponding to the pulleys 54 are exactly the same as the weights 58 corresponding to the pulleys 56. Each of the weights 58 pulls down one of the threads of the yarns 28 and 30 by equal load.

Accordingly, the yarn holding unit 34 is capable of holding the ends of the first yarns 28 and the ends of the second yarns 30 while all the threads of the yarns are pulled down by equal load. Similarly, the yarn holding unit 36 is capable of holding the other ends of the first yarns 28 and the other ends of the second yarns 30 while all the threads of the yarns are pulled down by equal load.

When the durability measurement for the test piece shown in FIG. 2 is performed by using the knitted yarns durability tester 32, the movable pressure pin 42 of the vibration unit 38 is vibrated to the knitted yarn portion 26 while the ends of the first yarns 28 and the ends of the second yarns 30 are held and pulled down by equal load. Therefore, the knitted yarns durability tester 32 allows the knitted yarn portion 26 to be vibrated while the tensile force acting on all the threads in the knitted yarn portion 26 are maintained to be uniform. Since no stress concentration on the knitted yarn portion 26 occurs, damaging some local areas of the knitted yarn portion 26 due to the durability measurement is avoided. Accordingly, when the knitted yarns durability tester 32 is used, it is possible to efficiently and precisely measure the individual durabilities of test pieces having different intersecting angles so as to determine the optimal value of the intersecting angle of the knitted yarn portion against the repeated tension and slacking and the repeated friction between the yarns.

In the knitted yarns durability tester 32 of the present embodiment, the yarn holding units 34 and 36 are, as shown in FIG. 3, arranged on frame rails 60 and 62. The pulley base 46 and the pulley base 66 are fixed to the frame rails 60 and 62. The movable base 44 and the movable base 64 are movable supported on the frame rails 60 and 62. Thus, the movable base 44 of the yarn holding unit 34 and the movable base 64 of the yarn holding unit 36 are movable along the lines of the frame rails 60 and 62.

The movable base 44 has a lock sleeve 68 provided thereon, and the movable base 64 has a lock sleeve 70 provided thereon. The movable base 44 is connected to the frame rails 60 and 62 through the lock sleeve 68. The lock sleeve 68 fixes the movable base 44 to the frame rails 60 and 62 when the lock sleeve 68 is set at its lock position. When the lock sleeve 68 is set at its unlock position, the movable base 44 is unlocked so that it is freely movable on the frame rails 60 and 62.

Similarly, the movable base 64 is connected to the frame rails 60 and 62 through the lock sleeve 60. The lock sleeve 70 fixes the movable base 64 to the frame rails 60 and 62 when the lock sleeve 60 is set at its lock position. When the lock sleeve 70 is set at its unlock position, the movable base 64 is unlocked so that it is freely movable on the frame rails 60 and 62.

Accordingly, when the lock sleeves 68 and 70 are set at the unlock positions, the first and second positions of the yarn holding units 34 and 36 relative to the knitted yarn portion 26 can be freely moved to different positions. When the lock sleeves 68 and 70 are set at the lock positions, the yarn holding units 34 and 36 relative to the position of the knitted yarn portion 26 can be fixed.

In the present embodiment, the knitted yarn portion 26 in which the first yarns 28 and the second yarns 30 are intersected is held at the center of the knitted yarns durability tester. The position of the knitted yarn portion 26 is stationary. The movable base 44 on which the ends of the yarns are held and the movable base 64 on which the opposite ends of the yarns are held are symmetrically arranged on both sides of the knitted yarn portion 26. The greater the distance between the movable bases 44 and 64 is, the greater the intersecting angle Θ between the sets of the yarns 28 and 30 is. The smaller the distance between the movable bases 44 and 64 is, the smaller the intersecting angle Θ is. Accordingly, it is possible for the knitted yarns durability tester 32 to easily vary the intersecting angle Θ to a desired angle by adjusting at least one of the relative position of the yarn holding unit 34 and the relative position of the yarn holding unit 36 by setting the lock sleeves 68 and 70. Therefore, it is unnecessary to prepare a number of test pieces of the knitted yarn portion having different intersecting angles prior to the durability measurement.

As shown in FIG. 3, the knitted yarn portion 26 is formed by interlacing the yarns 28-1 through 28-10 and the yarns 30-1 through 30-10 in the predetermined pattern. The knitted positions of the yarns in the knitted yarn portion 26 may deviate due to the vibrations when the durability measurement is being performed.

In the present embodiment, a stopper 72 which encloses the knitted yarn portion 26 therein is fixed to the knitted yarns durability tester 32 as shown in FIG. 3, in order to eliminate the above-mentioned problem. The stopper 72 is configured so that it is in accordance with the outside configuration of the knitted yarn portion 26. When the durability measurement is performed by using the knitted yarns durability tester 32, the knitted yarn portion 26 of the test piece is enclosed by the stopper 72. Therefore, the intersecting angle Θ of the test piece during the durability measurement is not changed, and the deviation of the knitted positions in the knitted yarn portion 26 is avoided. It is possible to make the result of the durability measurement highly reliable.

Figure 7:
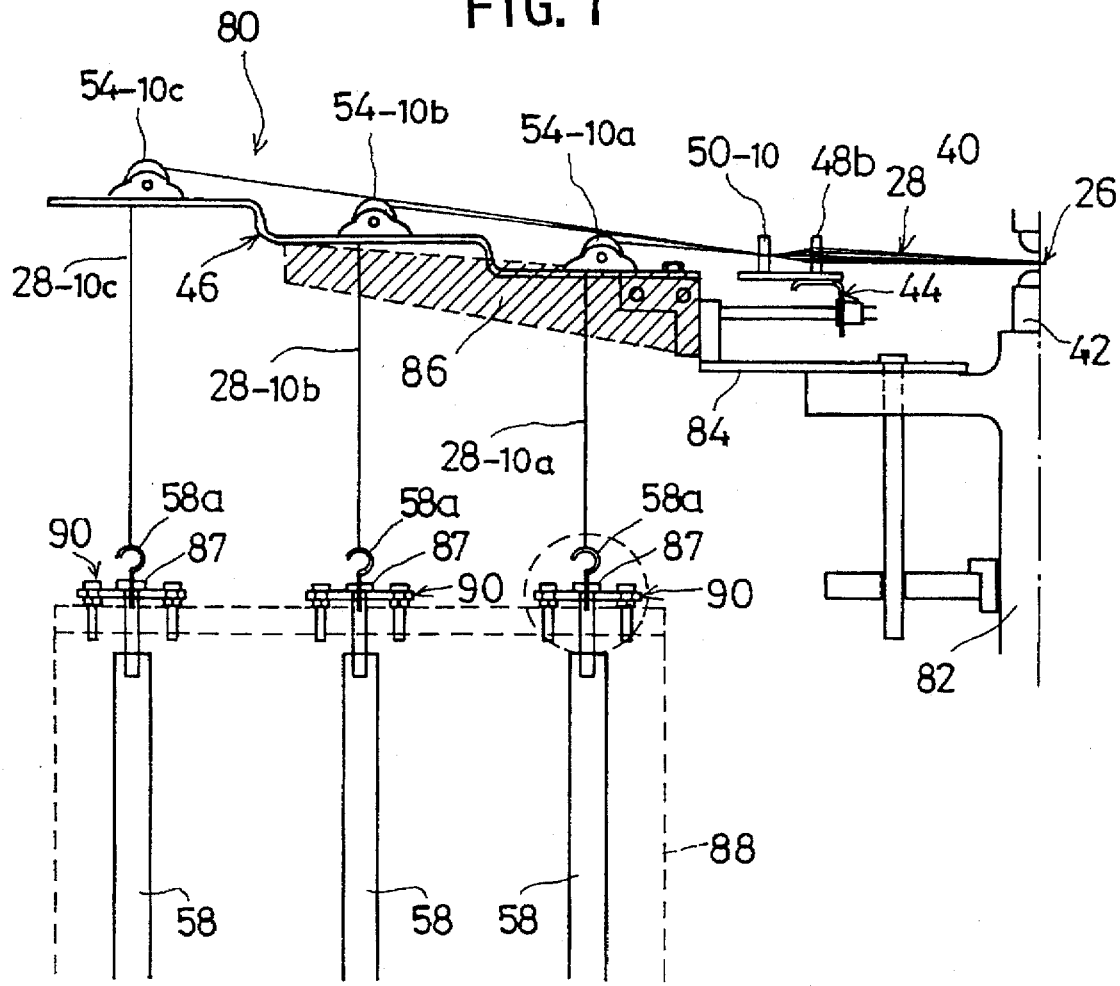
FIG. 7 is a side view of a knitted yarns durability tester in another embodiment of the present invention.

FIG. 7 shows a knitted yarns durability tester 80 in another embodiment of the present invention. In FIG. 7, the elements which are the same as corresponding elements in FIGS. 3 through 6 are designated by the same reference numerals, and a description thereof will be omitted.

In the present embodiment, the yarn holding unit 34 and the yarn holding unit 36 have essentially the same structure, and they are symmetrically arranged with respect to the position of the knitted yarn portion 26. For the sake of convenience, only the yarn holding unit 34 of the knitted yarns durability tester 80 is shown in FIG. 7 and will be described below. The yarn holding unit 36 thereof is not shown in FIG. 7, and a description of the yarn holding unit 36 will be omitted.

Referring to FIG. 7, the knitted yarns durability tester 80 includes a vibration unit 82, a connecting frame 84, and a reinforcing plate 86, in addition to the elements of the knitted yarns durability tester 32 of the previous embodiment. In the knitted yarns durability tester 80, the yarn holding unit 34 is fixed to the vibration unit 82 by the connecting frame 84 and the reinforcing plate 86. Similarly, the yarn holding unit 36 is fixed to the vibration unit 82 in the same manner.

The movable pressure pin 42 is attached to the vibration unit 82. The vibration unit 82 is connected to a vibration source (not shown) of the tester 80. The pulley base 46 is connected to the vibration unit 82 by the connecting frame 84. The reinforcing place 86 strengthens the connection between the connecting frame 84 and the pulley base 46.

In the knitted yarns durability tester 80, the vibrations by the vibration unit 82 are transmitted to the pulley base 46 as well as the movable pressure pin 42.

When the durability measurement for the knitted yarn portion 26 is performed by using the knitted yarns durability tester 80, the movable pressure pin 42 and the pulley base 46 are vibrated in the up and down directions by the vibration unit 82.

Similarly to the previous embodiment of FIG. 6, the knitted yarns durability tester 80 includes a plurality of weights 58 which are attached to the leading edges of the threads of the yarns from the knitted yarn portion 26, respectively. A hook 58a and a supporting member 87 are attached to the upper end of each weight 58.

Further, the knitted yarns durability tester 80 includes a casing 88 which supports the plurality of the weights 58 thereon. A plurality of weight position adjusting members 90 are provided on the casing 88. The weight position adjusting members 90 provided on the casing 88 correspond to the weights 58 one to one.

Figure 8:
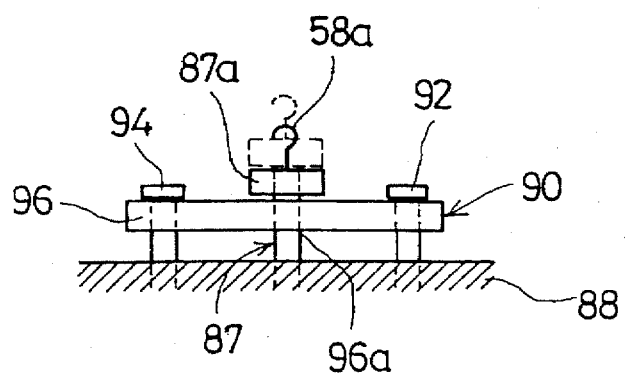
FIG. 8 is a side view of a weight position adjusting member of the knitted yarns durability tester in FIG. 7.

FIG. 8 shows one of the weight position adjusting members 90 of the knitted yarns durability tester 80 in FIG. 7.

Referring to FIG. 8, the weight position adjusting member 90 includes adjusting bolts 92 and 94, fastened to the casing 88, and a supporting plate 96 through which the adjusting bolts 92 and 94 are passed. The heads of the adjusting bolts 92 and 94 are supported on the supporting plate 96. The distance between the supporting plate 96 and the top of the casing 88 is adjustable by adjusting the fastening of the adjusting bolts 92 and 94 to the casing 88.

The adjusting plate 96 has a through hole 96a through which the supporting member 87 of the weight 58 is passed. The supporting member 87 is inserted into the through hole 96a of the adjusting plate 96. A stopper 87a is attached to an upper end of the supporting member 87. The stopper 87a has an outside diameter greater than an inside diameter of the through hole 96a of the supporting plate 96. When the stopper 87a of the supporting member 87 is in contact with the supporting plate 96, a further downward movement of the weight 58 is restricted.

As described above, in the present embodiment, the vibrations by the vibration unit 82 are transmitted to the pulley base 46 as well as the movable pressure pin 42. When the vibration unit 82 is at the lower dead center, the pulley base 46 is at the lowermost position. All the weight position adjusting members 90 on the casing 88 are arranged such that the stoppers 87a are just in contact with the supporting plates 96 and the threads pulled down by the weights 58 has no slacking portion when the pulley base 46 is at the lowermost position.

In the present embodiment, the moment the vibration unit 82 is at the lower dead center, the loads of the weights 58 do not act on the yarns of the knitted yarn portion 26 as the tensile stresses. When the vibration unit 82 moves up from the lower dead center, the pulley base 46 moves up relative to the casing 88. The weights 58 are pulled up from the casing 88 by the threads of the yarns of the knitted yarn portion 26. The loads of the weights 58 at this time act on the yarns of the knitted yarn portion 26 as the tensile stresses when the knitted yarn portion 26 is compressed by the movable pressure pin 42.

When the knitted yarns durability tester 80 of the present embodiment is used to perform the durability measurement for the knitted yarn portion 26, it is possible that the yarns of the knitted yarn portion are subjected to the repeated tensile stresses when the vibration unit 82 moves up from the lower dead center and they are not subjected to the tensile stresses the moment the vibration unit 82 is at the lower dead center.

In comparison with the knitted yarns durability tester 32 of the previous embodiment, the testing condition in which the knitted yarn portion 26 of the test piece is subjected to the compression by the movable pressure pin 42 of the tester 80, and in which the yarns of the knitted yarn portion 26 are at the same time subjected to the tensile stresses by the weights 58 is more approximate to the actual condition in which the knitted yarn portions 16 and 20 of the brake hose 10 on the vehicle are subjected to the stresses to expand the inside diameter of the hydraulic passage 24 when the brake fluid is fed through the brake hose 10. Therefore, it is possible for the knitted yarns durability tester 80 to efficiently and precisely measure individual durabilities of different test pieces having different intersecting angles, thus determining the optimal value of the intersecting angle for the knitted yarn portion 26 from the results of the durability measurement.

The above-described knitted yarns durability testers 32 and 80 of the present invention provide the following advantages when performing the durability measurement for the knitted yarn portion 26.

If the kinds of the first yarns 28 and the second yarns 30 of the test pieces are changed, it is possible to measure the individual durabilities of the test pieces including the first yarns 28 and the second yarns 30 which are different kinds.

If the mass of the weights 58 connected to the first yarns 28 and the mass of the weights 58 connected to the second yarns 30 are changed so that they are different from each other, it is possible to measure the individual durabilities of the test pieces when the first yarns 28 and the second yarns 30 are subjected to different quantities of the tensile stresses.

It is possible to measure the individual durabilities of the test pieces when the knitted yarn portion 26 of each test piece is subjected to the compression by the vibration unit 42 and the yarns of the knitted yarn portion 26 are at the same time subjected to the tensile stresses by the weights 58.

If the arrangement of the weight position adjusting members 90 of the knitted yarns durability tester 80 is modified, it is possible to measure the individual durabilities of the test pieces when the knitted yarn portion 26 of each test piece and the yarns of the knitted yarn portion 26 are subjected to the compression and to the tensile stresses, independently of each other.

As described above, it is possible that the knitted yarns durability testers 32 and 80 of the present invention easily provide the results of the durability measurement when the testing condition is changed to be in conformity with the predicted operating condition.

Further, the present invention is not limited to the above-described embodiments, and variations and modifications may be made without departing from the scope of the present invention.

For example, in the above-described embodiments, the movable base 44 holds the ends of the first yarns 28 and the ends of the second yarns 30 at the first positions relative to the knitted yarn portion 26, the movable base 64 holds the opposite ends of the first yarns 28 and the opposite ends of the second yarns 30 at the second positions relative to the knitted yarn portion 26, and the lock sleeves 68 and 70 and the frame rails 60 and 62, which are connected to the movable base 44 and the movable base 64, allow at least one of the first positions of the movable base 44 and the second positions of the movable base 64 to be moved along the lines of the frame rails 60 and 62 such that they are approached or separated. The above-described embodiments thus make it possible to vary the intersecting angle e of the yarns of the knitted yarn portion 26 to a desired angle.

However, according to the present invention, if at least one of the relative positions of the yarn pins 48a and 48b to the knitted yarn portion 26 and the relative positions of the yarn pins 48c and 48d to the knitted yarn portion 26 are changed, it is possible to vary the intersecting angle $\Theta$ of the knitted yarn portion 26. The relative positions of the yarn pins 48a and 48b and the relative positions of the yarn pins 48c and 48d can be moved in the transverse directions (the up/down directions in FIG. 3) in another embodiment of the present invention, rather than in the longitudinal directions (the right/left directions in FIG. 3) along the lines of the frame rails 60 and 62.

Further, in the above-described embodiments, the knitted yarn portion 26 is formed by intersecting the set of the first yarns 28 and the set of the second yarns 30, and the durability measurement for the knitted yarn portion 26 is performed. However, the knitted yarn durability tester according to the present invention can be applied to the durability measurement for another type of the knitted yarn portion, which is formed by intersecting three or more sets of yarns, for example. Obviously, it is possible to provide the knitted yarns durability tester in such a case with holding units for holding the ends of the yarns of the knitted yarn portion of the another type and a position adjusting unit for varying the respective intersecting angles between the sets of the yarns of the knitted yarn portion.

Figure 9:
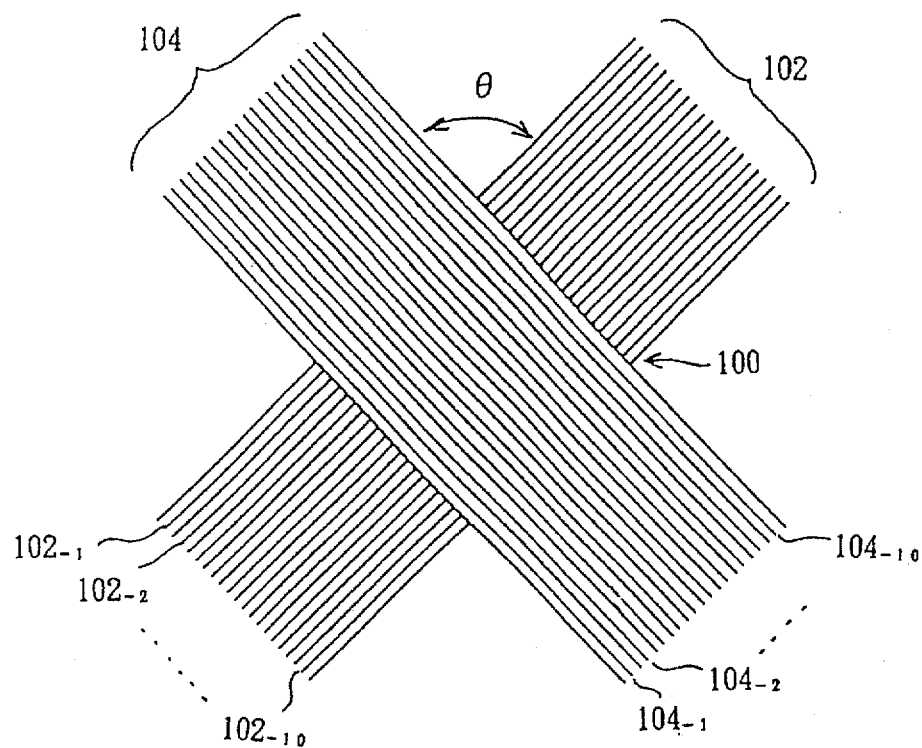
FIG. 9 is an enlarged view of another test piece which is subjected to durability measurement by the knitted yarns durability tester of the present invention.

FIG. 9 shows another test piece which is subjected to the durability measurement by the knitted yarns durability testers 32 and 80 of the above-described embodiments.

Referring to FIG. 9, the test piece has a knitted yarn portion 100 in which a set of first yarns 102 and a set of second yarns 104 are intersected merely in an overlaying manner. The first yarn set includes ten yarns 102-1 through 102-10, and the second yarn set includes ten yarns 104-1 through 104-10. The knitted yarn portion 100 is formed by intersecting the first yarns 102 and the second yarns 104 at an intersecting angle $\Theta$ and by merely overlaying the second yarn set on the first yarn set.

The knitted yarn portion 100 in the present embodiment is applied to the brake hose 10, as follows. The knitted yarn portion 16 of the brake hose 10 is formed by winding the first yarns 102 on the inner rubber hose 14 and further winding the second yarns 104 on the first yarns in the overlaying manner so as to form the intersecting angle Θ. Similarly, the knitted yarn portion 20 of the brake hose 10 is formed by winding the first yarns 102 on the intermediate rubber hose 18 and further winding the second yarns 104 on the first yarns 102 in the overlaying manner so as to form the intersecting angle Θ.

In the knitted yarn portion 100 of the present embodiment, each of the yarns 102-1 through 102-10 and the yarns 104-1 through 104-10 is a strand of three twisted threads, similarly to the knitted yarn portion 26 of the previous embodiment. The yarns 102-1 through 102-5, or one half of the first yarns of the knitted yarn portion 100, are connected to or wound on the yarn pin 48a, and they are further connected to the yarn pins 50-1 through 50-5 separately. The yarns 102-6 through 102-10, or the remainder of the first yarns of the knitted yarn portion 100, are connected to or wound on the yarn pin 48b, and they are further connected to the yarn pins 50-6 through 50-10 respectively. The threads of the above yarns 102-1 through 102-10 are tied to the weights 58 via the pulleys 54-1a through 54-10c.

Similarly, the yarns 104-1 through 104-5, or one half of the second yarns of the knitted yarn portion 100, are connected to or wound on the yarn pin 48c, and they are further connected to the yarn pins 52-1 through 52-5 respectively. The yarns 104-6 through 104-10, or the remainder of the second yarns of the knitted yarn portion 100, are connected to or wound on the yarn pin 48d, and they are further connected to yarn pins 52-6 through 52-10 respectively. The threads of the above yarns 104-1 through 104-10 are tied to the weights 58 via the pulleys 56-1a through 56-10c.

Accordingly, it is possible that the knitted yarns durability testers 32 and 80 of the above embodiments efficiently and precisely measure individual durabilities of different test pieces of the knitted yarn portion 100 having different intersecting angles. Therefore, it is possible to determine the optimal value of the intersecting angle for the knitted yarn portion 100 from the results of the durability measurement.

Figure 10:
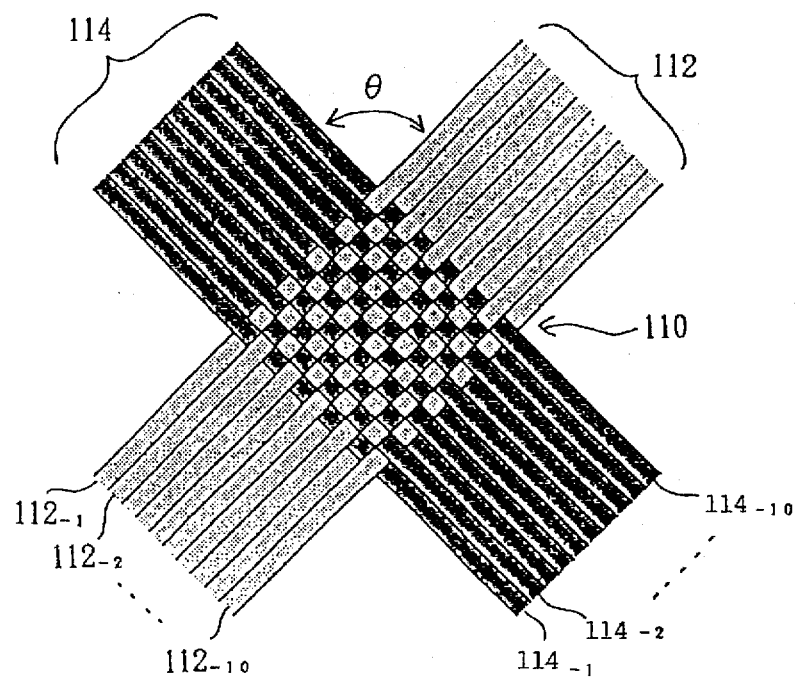
FIG. 10 is an enlarged view of a further test piece which is subjected to durability measurement by the knitted yarns durability tester of the present invention.

FIG. 10 shows a further test piece which is subjected to the durability measurement by the knitted yarns durability testers 32 and 80.

Referring to FIG. 10, the test piece has a knitted yarn portion 110 in which a set of first yarns 112 and a set of second yarns 114 are intersected, or regularly interlaced for every yarn. The first yarn set includes ten yarns 112-1 through 112-10, and the second yarn set includes ten yarns 114-1 through 114-10. The knitted yarn portion 110 is formed by regularly interlacing the first yarns 112 and the second yarns 114 for every yarn so as to form an intersecting angle Θ between the first yarns 112 and the second yarns 114.

The knitted yarn portion 110 in the present embodiment is utilized in the brake hose 10, as follows. The knitted yarn portion 16 of the brake hose 10 is formed by winding the yarns of the first yarn set 112 and the yarns of the second yarn set 114 on the inner rubber hose 14 such that they are regularly interlaced for every yarn so as to form the intersecting angle Θ. Similarly, the knitted yarn portion 20 of the brake hose 10 is formed by winding the yarns of the first yarn set 112 and the yarns of the second yarn set 114 on the intermediate rubber hose 18 such that they are regularly interlaced so as to form the intersecting angle Θ.

In the knitted yarn portion 110 of the present embodiment, each of the yarns 112-1 through 112-10 and the yarns 114-1 through 114-10 is a strand of three twisted threads. The yarns 112-1 through 112-5, or one half of the first yarns of the knitted yarn portion 110, are connected to or wound on the yarn pin 48a, and they are further connected to the yarn pins 50-1 through 50-5 separately. The yarns 112-6 through 112-10, or the remainder of the first yarns of the knitted yarn portion 110, are connected to or wound on the yarn pin 48b, and they are further connected to the yarn pins 50-6 through 50-10 respectively. The threads of the above yarns 112-1 through 112-10 are tied to the weights 58 via the pulleys 54-1a through 54-10c.

Similarly, the yarns 114-1 through 114-5, or one half of the second yarns of the knitted yarn portion 110, are connected to or wound on the yarn pin 48c, and they are further connected to the yarn pins 52-1 through 52-5 respectively. The yarns 114-6 through 114-10, or the remainder of the second yarns of the knitted yarn portion 110, are connected to or wound on the yarn pin 48d, and they are further connected to yarn pins 52-6 through 52-10 respectively. The threads of the above yarns 114-1 through 114-10 are tied to the weights 58 via the pulleys 56-1a through 56-10c.

Accordingly, it is possible that the knitted yarns durability testers 32 and 80 of the above embodiments efficiently and precisely measure individual durabilities of different test pieces of the knitted yarn portion 110 having different intersecting angles. Therefore, it is possible to determine the optimal value of the intersecting angle for the knitted yarn portion 110 from the results of the durability measurement.

What is claimed is:

1. A tester for measuring a durability of a knitted yarn portion in which at least two sets of yarns, including a set of first yarns and a set of second yarns, are intersected, said tester comprising:
   a first holding unit holding ends of said at least two sets of yarns at first positions relative to the knitted yarn portion;
   a second holding unit holding opposite ends of said at least two sets of yarns at second positions relative to the knitted yarn portion; and
   a position adjusting unit, connected to said first holding unit and said second holding unit, allowing at least one of said first positions and said second positions, relative to the knitted yarn portion, to be moved other positions, thus varying an intersecting angle of yarns of the knitted yarn portion; and
   a vibration unit having a fixed pin and a movable pressure pin, said movable pressure pin being vertically vibrated and subjecting the knitted yarn portion to the vibrations.

2. The tester according to claim 1, wherein said position adjusting unit comprises lock sleeves connected to said first holding unit and said second holding unit, said lock sleeves respectively locking said first holding unit and said second holding unit to said tester when said lock sleeves are set at lock positions, and respectively unlocking said first holding unit and said second holding unit when said lock sleeves are set at unlock positions.

3. The tester according to claim 1, further comprising frame rails on which said first holding unit and said second holding unit are movably supported, wherein said position adjusting unit allows at least one of said first positions and said second positions to be moved to other positions along the frame rails.

4. The tester according to claim 1, wherein said fixed pressure pin and said movable pressure pin are opposed to each other, the knitted yarn portion interposed between said fixed pressure pin and said movable pressure pin, said fixed pressure pin being fixed to the tester and contacted to the knitted yarn portion.

5. The tester according to claim 4, wherein said first holding unit and said second holding unit are both connected to said vibration unit, so that said first holding unit and said second holding unit are vibrated by said vibration unit when the knitted yarn portion is subjected to the vibrations by said vibration unit.

6. The tester according to claim 5, wherein said first holding unit comprises a plurality of pulleys on which all threads from the ends of said at least two sets of yarns are wound, and a plurality of weights which are tied to edges of said threads and pull said threads by equal load, and wherein said second holding unit comprises a plurality of pulleys on which all threads from the opposite ends of said at least two sets of yarns are wound, and a plurality of weights which are tied to edges of said threads and pull said threads by equal load.

7. The tester according to claim 6, wherein said first holding unit further comprises a plurality of weight position adjusting members which are attached to said weights of said first holding unit, and said second holding unit further comprises a plurality of weight position adjusting members which are attached to said weights of said second holding unit, said weight position adjusting members inhibiting the loads of the weights from acting on the yarns of the knitted yarn portion as tensile stresses when said vibration unit is at a lowermost position during the vibrations.

8. The tester according to claim 1, wherein said first holding unit comprises a plurality of pulleys on which all threads from the ends of said at least two sets of yarns are wound, and a plurality of weights which are tied to edges of said threads and pull said threads by equal load, and wherein said second holding unit comprises a plurality of pulleys on which all threads from the opposite ends of said at least two sets of yarns are wound, and a plurality of weights which are tied to edged of said threads and pull said threads by equal load.

9. The tester according to claim 1, wherein said first yarns and said second yarns of said knitted yarn portion are intersected in an overlaying manner.

10. The tester according to claim 1, wherein said first yarns and said second yarns of said knitted yarn portion are regularly interlaced for every yarn.

* * * * *